US010281263B2

(12) United States Patent
Krishnan

(10) Patent No.: US 10,281,263 B2
(45) Date of Patent: *May 7, 2019

(54) CRITICAL DIMENSION MEASUREMENTS WITH GASEOUS ADSORPTION

(71) Applicant: KLA-Tencor Corporation, Milpitas, CA (US)

(72) Inventor: Shankar Krishnan, Santa Clara, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/204,938

(22) Filed: Jul. 7, 2016

(65) Prior Publication Data
US 2017/0314913 A1 Nov. 2, 2017

Related U.S. Application Data

(60) Provisional application No. 62/330,751, filed on May 2, 2016.

(51) Int. Cl.
G01N 21/00 (2006.01)
G01B 11/22 (2006.01)
(Continued)

(52) U.S. Cl.
CPC .......... *G01B 11/22* (2013.01); *G01B 11/0641* (2013.01); *G01N 15/088* (2013.01); *G01N 21/00* (2013.01); *G01B 2210/56* (2013.01)

(58) Field of Classification Search
CPC ............. G01N 21/211; G01N 21/9501; G01N 21/956; G01B 11/02; G01B 11/046;
(Continued)

(56) References Cited

U.S. PATENT DOCUMENTS 4,568,565 A * 2/1986 Gupta ..................... C23C 16/42
204/157.41
5,399,379 A * 3/1995 Sandhu ................... C23C 16/34
257/E21.584
(Continued)

FOREIGN PATENT DOCUMENTS

JP 2010016279 A 1/2010
KR 10-1306986 B1 9/2013

OTHER PUBLICATIONS http://www.sigmaaldrich.com/catalog/product/aldrich/z553360?lang=en&region=US.
(Continued)

*Primary Examiner* — Hoa Q Pham
(74) *Attorney, Agent, or Firm* — Spano Law Group; Joseph S. Spano

(57) ABSTRACT

Methods and systems for performing optical measurements of geometric structures filled with an adsorbate by a gaseous adsorption process are presented herein. Measurements are performed while the metrology target under measurement is treated with a flow of purge gas that includes a controlled amount of fill material. A portion of the fill material adsorbs onto the structures under measurement and fills openings in the structural features, spaces between structural features, small volumes such as notches, trenches, slits, contact holes, etc. In one aspect, the desired degree of saturation of vaporized material in the gaseous flow is determined based on the maximum feature size to be filled. In one aspect, measurement data is collected when a structure is unfilled and when the structure is filled by gaseous adsorption. The collected data is combined in a multi-target model based measurement to reduce parameter correlations and improve measurement performance.

31 Claims, 8 Drawing Sheets

(51) Int. Cl.
*G01B 11/06* (2006.01)
*G01N 15/08* (2006.01)

(58) Field of Classification Search
CPC ............ G01B 11/0608; G01B 2210/56; G03F 7/70625; G03F 7/70608
USPC ........... 356/237.1–237.5, 601–635, 445–448
See application file for complete search history.

(56) References Cited

U.S. PATENT DOCUMENTS

| | | | |
|---|---|---|---|
| 5,608,526 | A | 3/1997 | Piwonka-Corle et al. |
| 5,859,424 | A | 1/1999 | Norton et al. |
| 6,429,943 | B1 | 8/2002 | Opsal et al. |
| 6,435,008 | B2 | 8/2002 | Baklanov et al. |
| 6,454,899 | B1 | 9/2002 | Campbell et al. |
| 6,633,831 | B2 | 10/2003 | Nikoonahad et al. |
| 6,684,172 | B1 | 1/2004 | Subramanian et al. |
| 6,734,967 | B1 | 5/2004 | Piwonka-Corle et al. |
| 6,816,570 | B2 | 10/2004 | Janik et al. |
| 6,895,075 | B2 | 5/2005 | Yokhin et al. |
| 6,897,157 | B2 * | 5/2005 | Liang .................... C23C 16/047 257/E21.03 |
| 6,972,852 | B2 | 12/2005 | Opsal et al. |
| 7,138,640 | B1 | 11/2006 | Delgado et al. |
| 7,196,782 | B2 * | 3/2007 | Fielden ................ G01N 21/211 257/E21.53 |
| 7,478,019 | B2 | 1/2009 | Zangooie et al. |
| 7,568,379 | B2 | 8/2009 | Simon et al. |
| 7,617,715 | B2 | 11/2009 | Georgeson et al. |
| 7,697,129 | B2 | 4/2010 | Haller |
| 7,755,764 | B2 | 7/2010 | Kwak et al. |
| 7,826,071 | B2 | 11/2010 | Shchegrov et al. |
| 7,907,264 | B1 | 3/2011 | Krishnan |
| 7,929,667 | B1 | 4/2011 | Zhuang et al. |
| 7,933,026 | B2 | 4/2011 | Opsal et al. |
| 9,556,521 | B1 * | 1/2017 | Prescop ................ H01J 37/305 |
| 10,145,674 | B2 * | 12/2018 | Krishnan ............ G03F 7/70616 |
| 2002/0078894 | A1 * | 6/2002 | Timmons ............ C23C 16/4481 118/726 |
| 2002/0142496 | A1 * | 10/2002 | Nakasuji .............. G01N 23/225 438/14 |
| 2003/0168594 | A1 | 9/2003 | Muckenhirn |
| 2005/0082482 | A1 * | 4/2005 | Ludviksson ............ C23C 14/54 250/342 |
| 2005/0115824 | A1 | 6/2005 | Donohue et al. |
| 2007/0034332 | A1 | 2/2007 | Muramoto |
| 2007/0158579 | A1 * | 7/2007 | Moors et al. ......... G03F 7/2043 250/423 R |
| 2008/0194074 | A1 * | 8/2008 | Jeon .................... H01L 21/0217 438/424 |
| 2009/0063077 | A1 | 3/2009 | Liu et al. |
| 2009/0081810 | A1 | 3/2009 | Hamada et al. |
| 2010/0235114 | A1 | 9/2010 | Levy et al. |
| 2011/0019207 | A1 | 1/2011 | Licitra et al. |
| 2011/0043795 | A1 * | 2/2011 | Den Boef ........ G01N 21/95623 356/237.2 |
| 2012/0268744 | A1 * | 10/2012 | Wolf .................. G01B 11/0625 356/447 |
| 2013/0026355 | A1 | 1/2013 | Climent |
| 2013/0114085 | A1 | 5/2013 | Wang et al. |
| 2014/0111791 | A1 | 4/2014 | Manassen et al. |
| 2014/0172394 | A1 | 6/2014 | Kuznetsov et al. |
| 2014/0222380 | A1 | 8/2014 | Kuznetsov et al. |
| 2014/0297211 | A1 | 10/2014 | Pandev et al. |
| 2014/0316730 | A1 | 10/2014 | Shchegrov et al. |
| 2014/0347666 | A1 * | 11/2014 | Veldman .............. G01N 21/211 356/369 |
| 2015/0042984 | A1 | 2/2015 | Pandev et al. |
| 2015/0046118 | A1 | 2/2015 | Pandev et al. |
| 2015/0076339 | A1 | 3/2015 | Federov |

OTHER PUBLICATIONS

A. Bourgeois, et al., "Description of the porosity of inhomogeneous porous low-k films using solvent adsorption studied by spectroscopic ellipsometry in the visible range," Thin Solid Films 455-456, 2004, pp. 366-369.

C. Negoro, "Nondestructive Characterization of a Series of Periodic Porous Silica Films by in situ Spectroscopic Ellipsometry in a Vapor Cell," Jap. J. of Appl. Phys., vol. 43, No. 4, 2004, pp. 1327-1329.

F.N. Dultsev, "Investigation of the microporous structure of porous layers using ellipsometric adsorption porometry", Thin Solid Films 458, 2004, pp. 137-142.

Dorian Zahorski, "Ellipsometry Porosimetry for Ultra Low K Material," Sopra Document EP-12, Jul. 2006.

R. H. Perry et al., Perry's Chemical Engineers' Handbook, 6th Ed., pp. 3-45, 3-64.

International Search Report dated Jul. 20, 2017, for PCT Application No. PCT/US2017/030290 filed on Apr. 29, 2017 by KLA-Tencor Corporation, 3 pages.

Arwin et al. Gas Sensing Based on Ellipsometric Measurement on Porous Silicon. Pysica Status Solidi (a), vol. 197, No. 2 May 26, 2003.

International Search Report dated Aug. 30, 2017, for PCT Application No. PCT/US2017/030246 filed on Apr. 28, 2017 by KLA-Tencor Corporation, 3 pages.

International Search Report dated Sep. 25, 2017, for PCT Application No. PCT/US2017/030267 filed on Apr. 28, 2017 by KLA-Tencor Corporation, 3 pages.

International Search Report dated Sep. 26, 2017, for PCT Application No. PCT/US2017/030309 filed on Apr. 29, 2017 by KLA-Tencor Corporation, 3 pages.

C. Himcinschi et al., "Ellipsometric study of the change in the porosity of silica xerogels after chemical modification to the surface with hexamethyldisilazane," Anal bioanal Chm (2002) 374: 654-657.

M.R. Baklanov, "Determination of pore size distribution in thin films by ellipsometric porosimetry," J. Vac. Sci. Technol. B 18(3), May/Jun. 2000, 1385-1391.

E. Skoczek, "Ellipsometric and Spectrophotometric Investigations of Porous Silica Thin Films Produced by Sol-Gel Method," Acta Physica Polonica A, vol. 120 No. 4 (2011), pp. 732-735.

Dorian Zahorski, "Ellipsometry Porosimetry for Ultra Low K Material," www.sopra-sa.com, UCLA, Jul. 2006.

* cited by examiner

| FILL MATERIAL | ΔH (J/MOLE) | ΔT ($T_A$=25°C, $P/P_O$ = 0.9) |
|---|---|---|
| WATER | 44,000 | -1.76 |
| TOLUENE | 38,200 | -2.02 |
| ETHANOL | 42,000 | -1.68 |

| FILL MATERIAL | MOLAR VOLUME (CC/MOLE) | SURFACE TENSION (DYNES/CM) |
|---|---|---|
| WATER | 18 | 73 |
| TOLUENE | 106.3 | 28.4 |
| ETHANOL | 57.62 | 22.1 |

CRITICAL DIMENSION MEASUREMENTS WITH GASEOUS ADSORPTION

CROSS REFERENCE TO RELATED APPLICATION

The present application for patent claims priority under 35 U.S.C. § 119 from U.S. provisional patent application Ser. No. 62/330,751, entitled "Porosity and Critical Dimension Measurements Using Gaseous Adsorption," filed May 2, 2016, the subject matter of which is incorporated herein by reference in its entirety.

TECHNICAL FIELD

The described embodiments relate to metrology systems and methods, and more particularly to methods and systems for improved measurement of structures fabricated in the semiconductor industry.

BACKGROUND INFORMATION

Semiconductor devices such as logic and memory devices are typically fabricated by a sequence of processing steps applied to a specimen. The various features and multiple structural levels of the semiconductor devices are formed by these processing steps. For example, lithography among others is one semiconductor fabrication process that involves generating a pattern on a semiconductor wafer. Additional examples of semiconductor fabrication processes include, but are not limited to, chemical-mechanical polishing, etch, deposition, and ion implantation. Multiple semiconductor devices may be fabricated on a single semiconductor wafer and then separated into individual semiconductor devices.

Metrology processes are used at various steps during a semiconductor manufacturing process to detect defects on wafers to promote higher yield. Model-based metrology techniques offer the potential for high throughput without the risk of sample destruction. A number of model-based metrology based techniques including scatterometry, ellipsometry, and reflectometry implementations and associated analysis algorithms are commonly used to characterize critical dimensions, film thicknesses, composition, overlay and other parameters of nanoscale structures.

Modern semiconductor processes are employed to produce complex structures. A complex measurement model with multiple parameters is required to represent these structures and account for process and dimensional variations. Complex, multiple parameter models include modeling errors induced by parameter correlations and low measurement sensitivity to some parameters. In addition, regression of complex, multiple parameter models having a relatively large number of floating parameter values may not be computationally tractable.

To reduce the impact of these error sources and reduce computational effort, a number of parameters are typically fixed in a model-based measurement. Although fixing the values of a number of parameters may improve calculation speed and reduce the impact of parameter correlations, it also leads to errors in the estimates of parameter values.

Currently, the solution of complex, multiple parameter measurement models often requires an unsatisfactory compromise. Current model reduction techniques are sometimes unable to arrive at a measurement model that is both computationally tractable and sufficiently accurate. Moreover, complex, multiple parameter models make it difficult, or impossible, to optimize system parameter selections (e.g., wavelengths, angles of incidence, etc.) for each parameter of interest.

Future metrology applications present challenges due to increasingly small resolution requirements, multi-parameter correlation, increasingly complex geometric structures, and increasing use of opaque materials. Thus, methods and systems for improved measurements are desired.

SUMMARY

Methods and systems for performing optical measurements of geometric structures filled with an adsorbate by a gaseous adsorption process are presented herein. Measurements are performed while the local environment around the metrology target under measurement is treated with a flow of purge gas that includes a controlled amount of fill material. A portion of the fill material (i.e., the adsorbate) adsorbs onto the structures under measurement (i.e., the adsorbent structures) and fills openings in the structural features, spacing between structural features, small volumes such as notches, trenches, slits, contact holes, etc.

In one aspect, the desired degree of saturation of vaporized material in the gaseous flow provided to the structures under measurement is determined based on the maximum feature size to be filled by gaseous adsorption.

In another aspect, model based measurements are performed with a data set including measurement signals collected from a metrology target having geometric features filled with an adsorbate. The presence of the adsorbate changes the optical properties of the structure under measurement compared to a measurement scenario where the purge gas is devoid of any fill material.

In some examples, multiple measurements of the metrology target are performed for different adsorption states. Each measurement corresponds to a different amount of adsorbate adsorbed onto the structures under measurement. By collecting measurement signal information associated with a metrology target having geometric features filled with different amounts of adsorbate, parameter correlation among floating measurement parameters is reduced and measurement accuracy is improved.

In some examples, measurement data is collected when a structure is filled from gaseous adsorption and measurement data is collected from the same structure when the structure is not filled (i.e., not subject to gaseous adsorption). The collected data is combined in a multi-target model based measurement to improve measurement performance.

In some embodiments, the amount of fill material vaporized in a gaseous flow provided to the structures under measurement is regulated by controlling the vapor pressure of the fill material. In some embodiments, a purge gas is bubbled through a liquid bath of fill material. The partial pressure of the fill material vaporized in the purge gas flow is equal to the equilibrium pressure of the fill material over the liquid bath of the fill material. The degree of saturation of the vaporized fill material at the wafer is controlled by maintaining the liquid bath temperature below the wafer temperature by a desired amount.

In some embodiments, the degree of saturation of the vaporized fill material at the wafer is controlled by adding an involatile solute in a liquid bath of fill material that suppresses the equilibrium vapor pressure of the fill material. In these embodiments, the degree of saturation of the vaporized fill material is regulated by controlling the concentration of solute in solution.

The foregoing is a summary and thus contains, by necessity, simplifications, generalizations and omissions of detail; consequently, those skilled in the art will appreciate that the summary is illustrative only and is not limiting in any way. Other aspects, inventive features, and advantages of the devices and/or processes described herein will become apparent in the non-limiting detailed description set forth herein.

DETAILED DESCRIPTION

Reference will now be made in detail to background examples and some embodiments of the invention, examples of which are illustrated in the accompanying drawings.

Methods and systems for performing optical measurements of geometric structures filled with an adsorbate by a gaseous adsorption process are presented herein. Model based measurements are performed with an enriched data set including measurement signals collected from a metrology target having geometric features filled with an adsorbate. This reduces parameter correlation among floating measurement parameters and improves measurement accuracy. Thus, sufficiently accurate model-based measurement results can be obtained, and often with reduced computational effort.

Measurements are performed while the local environment around the metrology target under measurement is treated with a flow of purge gas that includes a controlled amount of fill material. A portion of the fill material (i.e., the adsorbate) adsorbs onto the structures under measurement (i.e., the adsorbent structures) and fills openings in the structural features, openings between structural features, etc. The presence of the adsorbate changes the optical properties of the structure under measurement compared to a measurement scenario where the purge gas is devoid of any fill material. In some examples, multiple measurements of the metrology target are performed for different adsorption states. In other words, each measurement corresponds to a different amount of adsorbate adsorbed onto the structures under measurement. By collecting measurement signal information associated with a metrology target having geometric features filled with different amounts of adsorbate, model based measurements are performed with an enriched set of measurement data.

In one example, measurement data is collected when a structure is unfilled and additional measurement data is collected when the same structure is filled by gaseous adsorption. The collected data is combined in a multi-target model based measurement to estimate the value of one or more parameters of interest with reduced parameter correlation and improved measurement performance.

Figure 1:
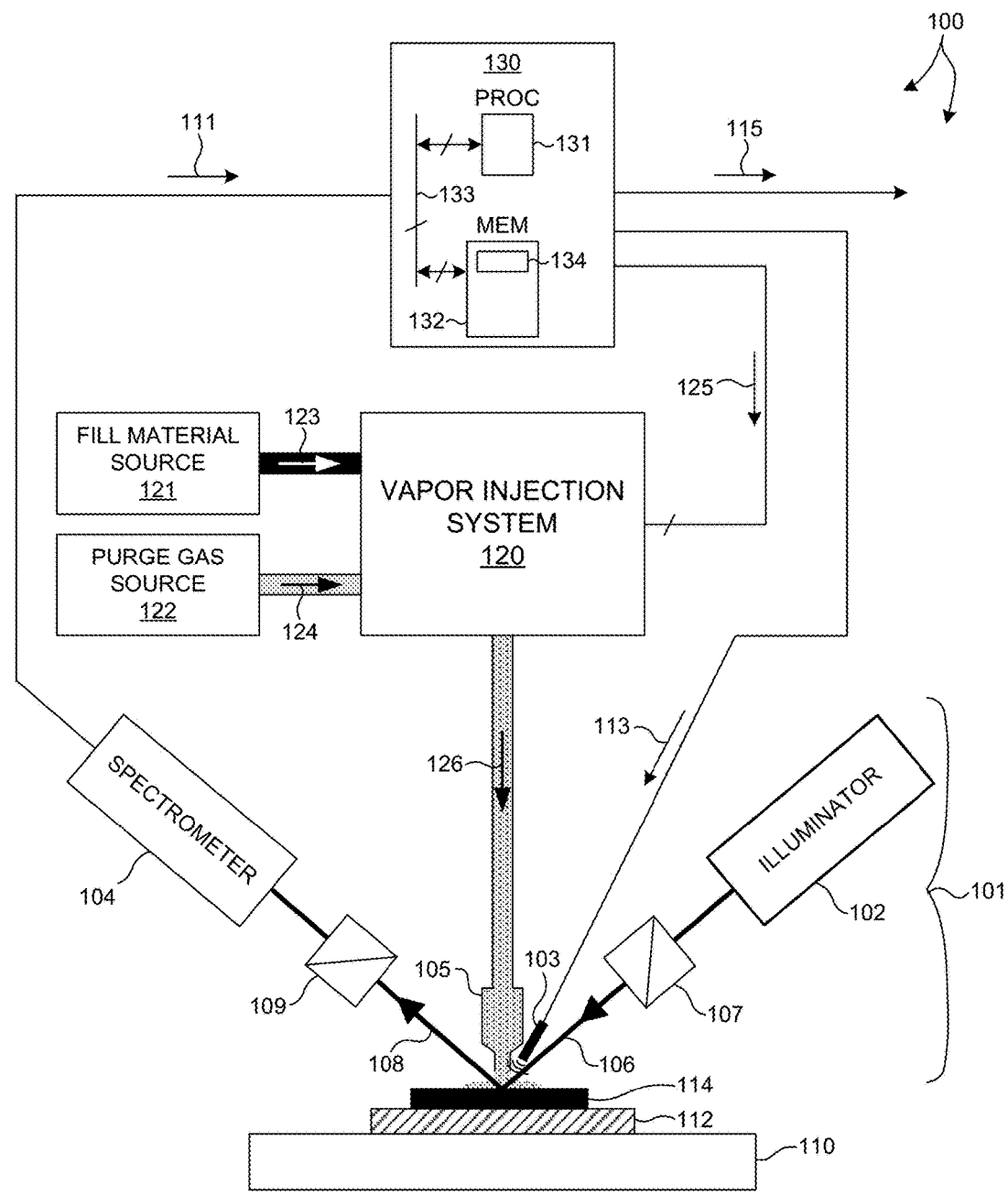
FIG. 1 is a diagram illustrative of a system 100 for measuring structures of a semiconductor wafer subject to gaseous adsorption.

FIG. 1 illustrates a system 100 for measuring characteristics of a semiconductor wafer. As shown in FIG. 1, the system 100 may be used to perform spectroscopic ellipsometry measurements of one or more structures 114 of a semiconductor wafer 112 disposed on a wafer positioning system 110. In this aspect, the system 100 may include a spectroscopic ellipsometer 101 equipped with an illuminator 102 and a spectrometer 104. The illuminator 102 of the system 100 is configured to generate and direct illumination of a selected wavelength range (e.g., 100-2500 nm)to the structure 114 disposed on the surface of the semiconductor wafer 112. In turn, the spectrometer 104 is configured to receive light from the surface of the semiconductor wafer 112. It is further noted that the light emerging from the illuminator 102 is polarized using a polarization state generator 107 to produce a polarized illumination beam 106. The radiation reflected by the structure 114 disposed on the wafer 112 is passed through a polarization state analyzer 109 and to the spectrometer 104. The radiation received by the spectrometer 104 in the collection beam 108 is analyzed with regard to polarization state, allowing for spectral analysis of radiation passed by the analyzer. The detected spectra 111 are passed to the computing system 130 for analysis of the structure 114.

Computing system 130 is configured to receive measurement data 111 associated with a measurement (e.g., critical dimension, film thickness, composition, process, etc.) of the structure 114 of specimen 112 that is filled due to gaseous adsorption. In one example, the measurement data 111 includes an indication of the measured spectral response of the specimen by measurement system 100 based on the one or more sampling processes from the spectrometer 104. In some embodiments, computing system 130 is further configured to determine specimen parameter values of structure 114 from measurement data 111. In one example, the computing system 130 is configured to access model parameters in real-time, employing Real Time Critical Dimensioning (RTCD), or it may access libraries of pre-computed models for determining a value of at least one parameter of interest associated with the target structure 114. In some embodiments, the estimated values of the one or more parameters of interest are stored in a memory (e.g., memory 132). In the embodiment depicted in FIG. 1, the estimated values 115 of the one or more parameters of interest are communicated to an external system (not shown).

In general, ellipsometry is an indirect method of measuring physical properties of the specimen under inspection. In most cases, the raw measurement signals (e.g., $\alpha_{meas}$ and $\beta_{meas}$) cannot be used to directly determine the physical properties of the specimen. The nominal measurement process consists of parameterization of the structure (e.g., film thicknesses, critical dimensions, material properties, etc.) and the machine (e.g., wavelengths, angles of incidence, polarization angles, etc.). A measurement model is created that attempts to predict the measured values (e.g., $\alpha_{meas}$ and $\beta_{meas}$). As illustrated in equations (1) and (2), the model includes parameters associated with the machine ($P_{machine}$) and the specimen ($P_{specimen}$).

$$\alpha_{model} = f(P_{machine}, P_{specimen}) \quad (1)$$

$$\beta_{model} = g(P_{machine}, P_{specimen}) \quad (2)$$

Machine parameters are parameters used to characterize the metrology tool (e.g., ellipsometer 101). Exemplary machine parameters include angle of incidence (AOI), analyzer angle ($A_O$), polarizer angle ($P_O$), illumination wavelength, numerical aperture (NA), compensator or waveplate (if present), etc. Specimen parameters are parameters used to characterize the specimen (e.g., specimen 112 including structures 114). For a thin film specimen, exemplary specimen parameters include refractive index, dielectric function tensor, nominal layer thickness of all layers, layer sequence, etc. For a CD specimen, exemplary specimen parameters include geometric parameter values associated with different layers, refractive indices associated with different layers, etc. For measurement purposes, the machine parameters are treated as known, fixed parameters and one or more of the specimen parameters are treated as unknown, floating parameters.

In some examples, the floating parameters are resolved by an iterative process (e.g., regression) that produces the best fit between theoretical predictions and experimental data. The unknown specimen parameters, $P_{specimen}$, are varied and the model output values (e.g., ($\alpha_{model}$ and $\beta_{model}$) are calculated until a set of specimen parameter values are determined that results in a close match between the model output values and the experimentally measured values (e.g., ($\alpha_{meas}$ and $\beta_{meas}$). In a model based measurement application such as spectroscopic ellipsometry on a CD specimen, a regression process (e.g., ordinary least squares regression) is employed to identify specimen parameter values that minimize the differences between the model output values and the experimentally measured values for a fixed set of machine parameter values.

In some examples, the floating parameters are resolved by a search through a library of pre-computed solutions to find the closest match. In a model based measurement application such as spectroscopic ellipsometry on a CD specimen, a library search process is employed to identify specimen parameter values that minimize the differences between pre-computed output values and the experimentally measured values for a fixed set of machine parameter values.

In a model-based measurement application, simplifying assumptions often are required to maintain sufficient throughput. In some examples, the truncation order of a Rigorous Coupled Wave Analysis (RCWA) must be reduced to minimize compute time. In another example, the number or complexity of library functions is reduced to minimize search time. In another example, the number of floating parameters is reduced by fixing certain parameter values. In some examples, these simplifying assumptions lead to unacceptable errors in the estimation of values of one or more parameters of interest (e.g., critical dimension parameters, overlay parameters, etc.). By performing measurements of structures subject to gaseous adsorption as described herein, the model-based measurement model can be solved with reduced parameter correlations and increased measurement accuracy.

As depicted in FIG. 1, metrology system 100 includes a vapor injection system 120 configured to provide a gaseous flow 126 to structure 114 during measurement. In one aspect, gaseous flow 126 includes a purge gas and a fill material vaporized in the purge gas. When the gaseous flow comes into contact with the structure 114, adsorption takes place and a portion of the fill material (i.e., the adsorbate) adsorbs onto structure 114 (i.e., the adsorbent) under measurement. The adsorbate fills at least a portion of one or more structural features of the structure 114. The presence of the adsorbate changes the optical properties of the measured structure.

In some embodiments, a measurement is performed when the purge gas flow does not include fill material (e.g., pure nitrogen gas or clean dry air), and another measurement is performed when the purge gas flow includes fill material such that the adsorbate completely fills the openings between the structural features under measurement. The measurement data collected from these two measurements is communicated to computing system 130 and an estimate of one or more structural parameters of interest is made based on both sets of measurement data.

In some embodiments, a series of measurements are performed under different adsorption conditions such that the amount of adsorption onto the structural features under measurement is different for each measurement. The measurement data collected from the series of measurements is communicated to computing system 130 and an estimate of one or more structural parameters of interest is made based on the collected measurement data.

As depicted in FIG. 1, an amount of fill material 123 is transported from a fill material source 121 to the vapor injection system 120. In addition, a flow of purge gas 124 is transported from a purge gas source 122 to the vapor injection system. Vapor injection system 120 causes fill material to vaporize into the flow of purge gas to generate the gaseous flow 126 provided to structure 114 under measurement. In the embodiment depicted in FIG. 1, the flow of purge gas and the amount of fill material vaporized into the flow of purge gas is controlled by command signals 125 communicated from computing system 130 to vapor injection system 120. Thus, command signals 125 control the desired composition of gaseous flow 126. As depicted in FIG. 1, gaseous flow 126 passes through nozzle 105 that directs gaseous flow 126 to the desired location on wafer 110 with the appropriate flow characteristics.

The embodiments of the system 100 illustrated in FIG. 1 may be further configured as described herein. In addition, the system 100 may be configured to perform any other block(s) of any of the method embodiment(s) described herein.

Figures 2, 3:
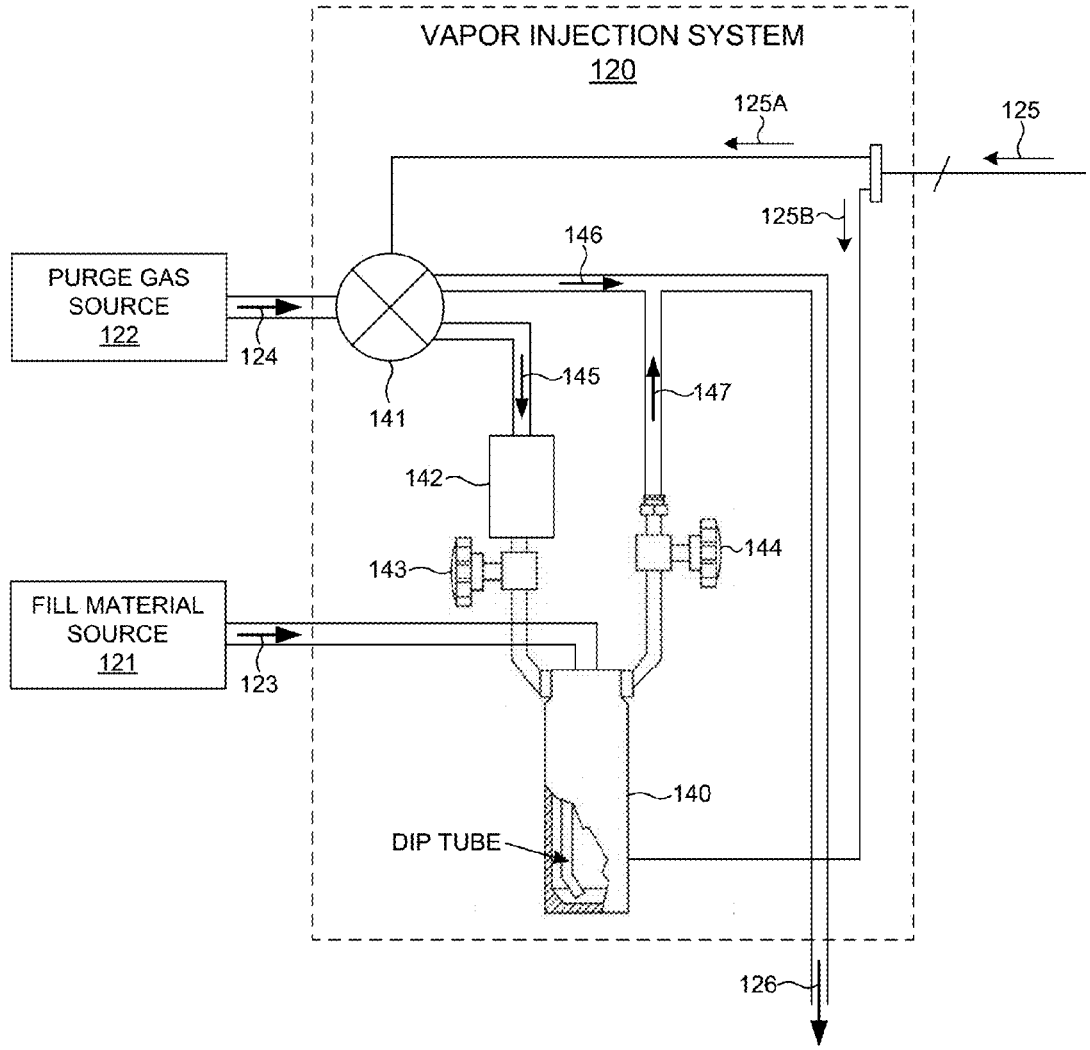
FIG. 2 is a diagram illustrative of a vapor injection system 120 of system 100 in one embodiment.
FIG. 3 depicts a table 127 including the enthalpy of vaporization, ΔH, of water, toluene, and ethanol. In addition, table 127 illustrates the difference between a wafer temperature and a temperature of a bath of liquid fill material to achieve a relative saturation of the fill material of 0.9 at the wafer.

FIG. 2 is a diagram illustrative of vapor injection system 120 in one embodiment. In this embodiment, the amount of fill material vaporized in the gaseous flow 126 provided to the wafer under measurement is regulated by controlling the vapor pressure of the fill material. In the embodiment depicted in FIG. 2, the partial pressure of the fill material vaporized in the purge gas flow 123 (e.g., nitrogen gas, clean, dry air, etc.) is equal to the equilibrium pressure of the fill material over a liquid bath of the fill material through which the purge gas is bubbled. In one example, a bubbler-type vapor injection system is a 1.2 liter capacity stainless steel bubbler, model 2553360, commercially available from Sigma-Aldrich, St. Louis, Mo. (USA).

As depicted in FIG. 2, the flow of purge gas 124 passes through a three-way valve 141. In some embodiments, three-way valve 141 proportions the portion 145 of purge gas flow 124 that flows through bubbler 140 with the portion 146 that does not flow through bubbler 140 based on a position of the three-way valve. In this manner, the amount of purge gas flow 124 into which fill material is vaporized is controlled by three-way valve 141. In the embodiment depicted in FIG. 2, signal 125A includes an indication of the desired position of three-way valve 141. In response, three-way valve 141 adjusts to the desired position, and thus, the desired proportion of purge gas flow into which fill material is vaporized. Portion 145 of purge gas flow 124 passes through a check valve 142, a flow control valve 143, and into bubbler 140. In bubbler 140, an amount of fill material is vaporized into the portion 145 of purge gas flow 124 to generate a gaseous flow 147 of purge gas and fill material. Gaseous flow 147 is combined with the portion 146 of purge gas that did not flow through bubbler 140 to generate gaseous flow 126.

In some embodiments, three-way valve 141 is controlled such that the entirety of purge gas flow 124 either flows through bubbler 140 or by-passes bubbler 140 completely and passes directly to the wafer as gaseous flow 126 based on a position of the three-way valve. In this manner, gaseous flow 126 is either a dry purge gas flow 124 having zero partial pressure of fill material or the entire purge gas flow 124 is subject to vaporization of fill material depending on the state of three-way valve 141.

As fill material is vaporized in bubbler 140 and carried away as gaseous flow 147, additional fill material 123 flows from fill material source 121 to maintain a constant fill level in bubbler 140. In some embodiments, the fill level is automatically controlled based on a level sensor and flow control scheme. In some other embodiments, the fill level is periodically maintained by a manual filling operation.

In one embodiment, the degree of saturation of the vaporized fill material at an ambient temperature, $T_a$, is controlled by maintaining the liquid bath at a temperature, T, below the ambient temperature. The relationship between equilibrium vapor pressure, $p_0$, of a pure substance and temperature, T, is given by the Clausius-Clapyron equation illustrated by equation (1), where $\Delta H$ is the enthalpy of vaporization of the pure substance and R is the ideal gas constant, which is 8.31 J/mole·° K.

$$\frac{d\ln(p_0)}{d\left(\frac{1}{T}\right)} = -\frac{\Delta H}{R} \quad (1)$$

Based on equation (1), the relative saturation, $p/p_0$, for a fill material saturated at a temperature, T, which is less than the ambient temperature, Ta, is illustrated by equation (2)

$$\ln\left(\frac{p}{p_0}\right) = \frac{\Delta H}{R}\left(\frac{1}{T_a} - \frac{1}{T}\right) \quad (2)$$

FIG. 3 depicts a table 127 including the enthalpy of vaporization, $\Delta H$, of water, toluene, and ethanol. Each of these substances may be suitable as fill materials as described herein. In addition, table 127 illustrates the difference between the ambient temperature (i.e., wafer temperature) and the bath temperature when the ambient temperature is 25 degrees Centigrade and the desired relative saturation of the fill material, $p/p_0$, is 0.9. As illustrated in table 127, by maintaining the bath temperature below the ambient temperature by the illustrated amounts, a partial pressure at 0.9 is maintained for each listed fill material. It may be advantageous to utilize any of these substances as fill materials because it is a relatively simple matter to maintain a temperature differential of approximately two degrees Centigrade between the wafer and the liquid bath of bubbler 140.

In some embodiments, the bath temperature and wafer temperature are measured and communicated to computing system 130. Computing system determines a difference between the wafer temperature and the bath temperature and calculates a desired wafer temperature, bath temperature, or both. In some embodiments, computing system 130 generates a command signal 125B indicative of a desired bath temperature to vapor injection system 120. In response, vapor injection system 120 adjusts the bath temperature to the desired value using a local heating or cooling unit (not shown). In some embodiments, computing system 130 generates a command signal (not shown) indicative of a desired wafer temperature to a wafer conditioning subsystem (not shown). In response, the wafer conditioning subsystem adjusts the wafer temperature to the desired value using a wafer heating or cooling unit (not shown). In some embodiments, computing system 130 generates a command signal 113 (depicted in FIG. 1) indicative of a desired wafer temperature to a local wafer heating element 103. In response, the heating unit 103 adjusts the wafer temperature locally (i.e., in the immediate vicinity of the measurement location) to the desired value using a radiative heating element.

In some embodiments, control of the temperature difference between the wafer and the bath is controlled by a computing system associated with vapor injection system 120. In this sense, control of the temperature difference between the wafer and the bath by computing system 130 is provided by way of non-limiting example. Any suitable control architecture and temperature regulation scheme may be contemplated within the scope of this patent document.

As described with reference to FIG. 2, the amount of fill material provided to the wafer under measurement is controlled by regulating the portion 145 of purge gas flow 124 that is subject to vaporization of fill material relative to the portion 146 of purge gas flow 124 that is not. In addition, the degree of saturation of the vaporized fill material at wafer temperature is controlled by regulating the difference between the wafer temperature and the bath temperature.

Figures 4, 5:
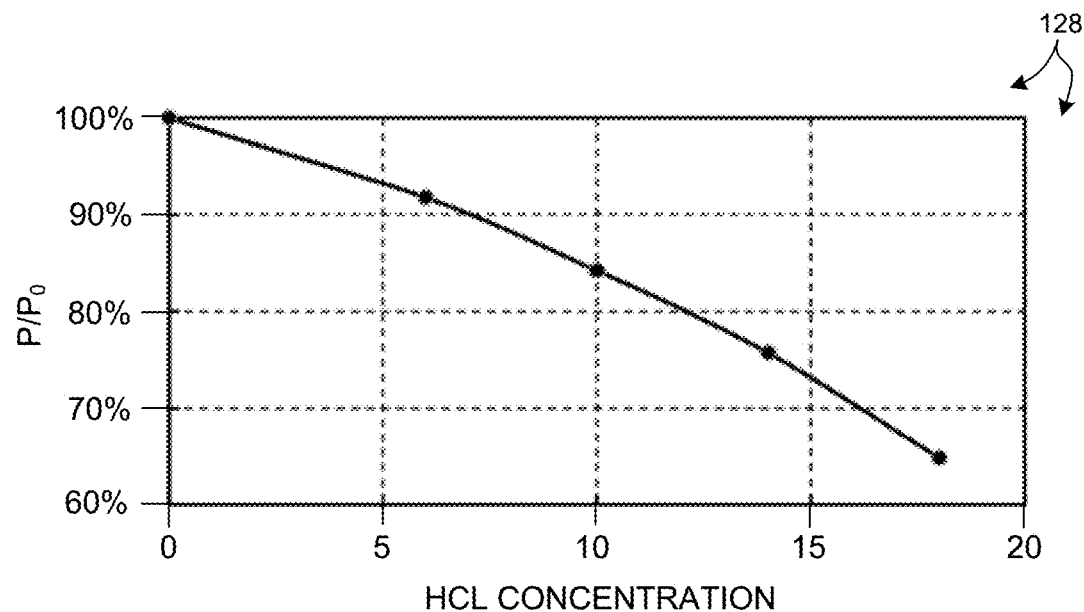
FIG. 4 depicts a plot 128 of the partial pressure of water as a function of concentration of hydrochloric acid in the bath of water.
FIG. 5 depicts a table 129 illustrating the molar volume and surface tension associated with water, toluene, and ethanol.

In another embodiment, the degree of saturation of the vaporized fill material at ambient temperature is controlled by adding an involatile solute in a liquid bath of solvent (i.e., fill material) that suppresses the equilibrium vapor pressure of the solvent compared to the equilibrium vapor pressure of the solvent alone. In one example, a solution formed from water as the solvent and an involatile solute (e.g., sodium chloride, hydrochloric acid, etc.) exhibits a vapor pressure of water that is less than the equilibrium vapor pressure of pure water. FIG. 4 depicts a plot 128 of the partial pressure of water as a function of concentration of hydrochloric acid in the bath of water. A similar result exists for a solution of sodium chloride dissolved in water. For example, a solution of six percent sodium chloride dissolved in water yields a relative humidity, $p/p_0$, of 90%.

In these embodiments, the degree of saturation of the vaporized fill material (i.e., the solvent) is regulated by controlling the concentration of solute in solution. In some embodiments, the amount of solvent in the bath is controlled to maintain the desired concentration, and thus the desired partial pressure of the vaporized solvent. In these embodiments, precise temperature control is not necessary as long as the bath temperature is maintained nominally at the ambient temperature (i.e., wafer temperature).

FIG. 1 depicts gaseous flow 126 provided locally to the metrology target under measurement. However, in general, gaseous flow 126 may be provided over the entire wafer, through any portion of the beam path from the illumination source to the detector, or any combination thereof. Various examples of providing purge gas flow over the wafer and through the beam path between the illumination source and the detector are described in U.S. Pat. No. 7,755,764, by Hidong Kwak, et al., and issued on Jul. 13, 2010, the subject matter of which is incorporated herein by reference in its entirety.

In general, any suitable purge gas and fill material may be selected for use in performing measurements as described herein. Exemplary purge gases include inert gases, nitrogen, and clean dry air. The selection of suitable purge gas is driven primarily by availability in a semiconductor fabrication facility. Exemplary fill materials include water, ethanol, and toluene. The selection of suitable fill materials is driven by the ability to control vapor pressure, void filling characteristics, optical characteristics, and any chemical interactions between the fill material and the specimen under measurement.

For example, both the index of refraction of the fill material and the absorption coefficient of the fill material are considered in the underlying measurement model as the liquid fill material not only refracts incident light, but also absorbs incident light. Both of these characteristics create differences between measurements performed with fill and measurements performed without fill, particularly at relatively short illumination wavelengths (e.g., vacuum ultraviolet wavelengths ranging from 120 nanometers to 190 nanometers). Thus, a selection of a liquid fill material that differs substantially from air in both index of refraction and absorption coefficient offers the opportunity for reduced parameter correlations in a multi-target measurement analysis.

In a further aspect, gaseous adsorption is employed to fill spaces between geometric, structural features of a metrology target itself (e.g., a critical dimension (CD) structures, grating structures, overlay structures, etc.) during measurement of the metrology target by adsorption (i.e., capillary condensation). In general, the desired degree of saturation of vaporized material in gaseous flow 126 is determined based on the maximum feature size to be filled by gaseous adsorption. Adsorption is employed to fill small features (e.g., small volumes such as notches, trenches, slits, contact holes, etc.) with an adsorbent. Kelvin's equation provides an approximation of the maximum feature size that can be filled for a particular fill material, partial pressure of the fill material, and ambient temperature (e.g., wafer temperature). Equation (3) illustrates Kelvin's equation for a condensed meniscus having two different radii, $r_1$ and $r_2$, where, R, is the ideal gas constant, $T_a$, is the ambient temperature, V, is the molar volume of the fill material, $\gamma$, is the surface tension constant associated with the fill material, and $p/p_0$, is the partial pressure of the fill material.

$$\frac{1}{r_1} + \frac{1}{r_2} = \frac{RT_a}{\gamma V} \ln\left(\frac{p}{p_0}\right) \quad (3)$$

FIG. 5 depicts a table 129 illustrating the molar volume and surface tension associated with water, toluene, and ethanol.

Figure 6:
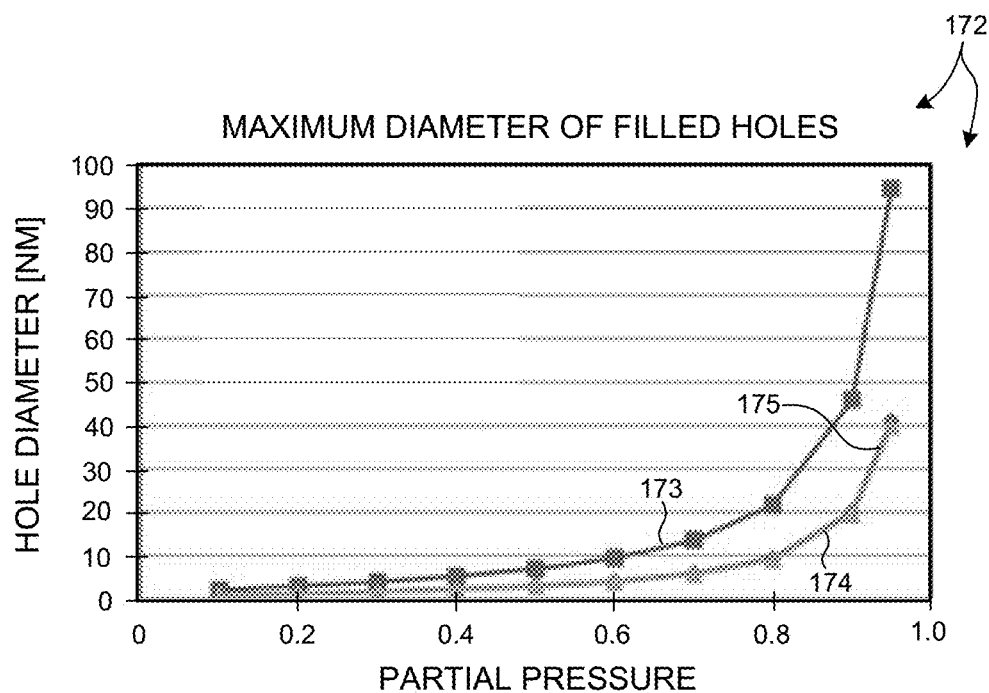
FIG. 6 depicts a plot 172 illustrating the maximum diameter of a cylindrical hole that can be filled by adsorption at different partial pressures in accordance with Kelvin's equation for water, ethanol, and toluene as fill materials.

For cylindrical hole features, $r_1$ equals $r_2$. FIG. 6 depicts a plot 172 illustrating the maximum diameter of a cylindrical hole that can be filled by adsorption in accordance with equation (3). Plot 172 depicts the maximum diameter of a cylindrical hole that can be filled by water (plotline 175), ethanol (plotline 174), and toluene (plotline 173) for various partial pressures of each fill material at an ambient temperature of 25 degrees Centigrade. As depicted in FIG. 6, cylindrical holes having diameters up to 40 nanometers may be filled when gaseous flow 126 is provided to the metrology target with a partial pressure of water or ethanol of 95% or higher. Also as depicted in FIG. 6, cylindrical holes having diameters up to 90 nanometers may be filled when gaseous flow 126 is provided to the metrology target with a partial pressure of toluene of 95% or higher.

Figure 7:
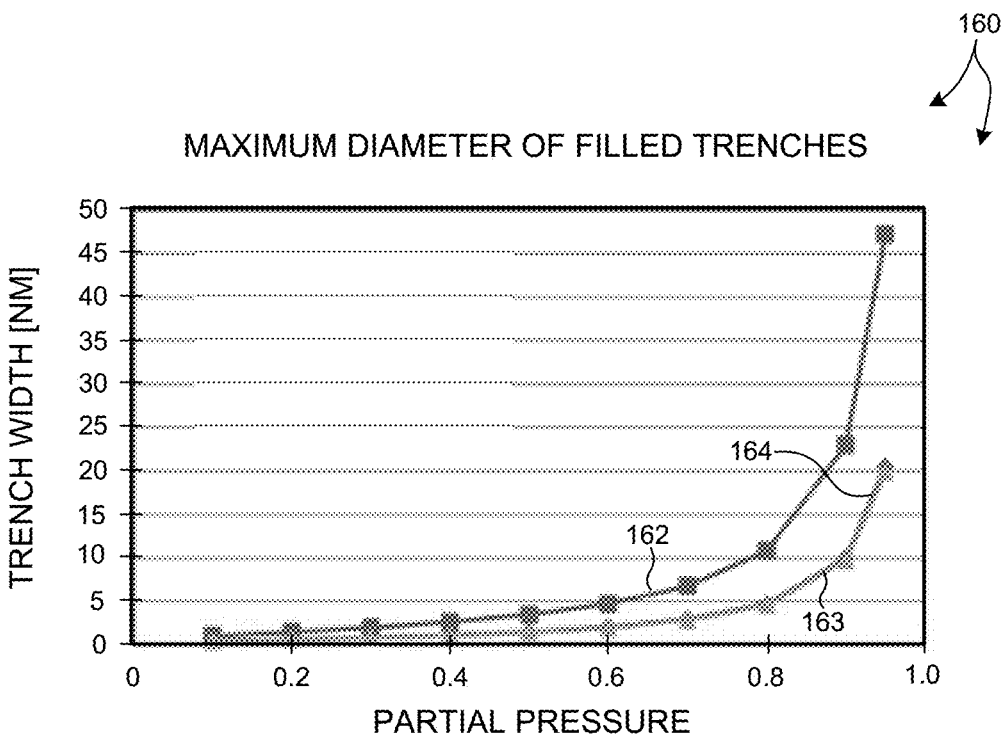
FIG. 7 depicts a plot 160 illustrating the maximum diameter of a long, trench-like feature that can be filled by adsorption at different partial pressures in accordance with Kelvin's equation for water, ethanol, and toluene as fill materials.

For lines and spaces, $r_2$, is zero. FIG. 7 depicts a plot 160 illustrating the maximum diameter of a long, trench-like feature that can be filled by adsorption in accordance with equation (3). Plot 160 depicts the maximum diameter of a trench that can be filled by water (plotline 164), ethanol (plotline 163), and toluene (plotline 162) for various partial pressures of each fill material at an ambient temperature of 25 degrees Centigrade. As illustrated, the maximum diameter across a long, trench-like feature is half the maximum diameter of a cylindrical hole feature. As depicted in FIGS. 6 and 7, the plotlines of water and ethanol appear to overlap because the performance of ethanol as a fill material is very similar to water.

In one aspect, the degree of saturation of the vaporized fill material at an ambient temperature, $T_a$, is adjusted such that all features below a desired maximum feature size are filled. In some embodiments, this is achieved by controlling the temperature difference between the wafer and the liquid bath of fill material. In some other embodiments, this is achieved by controlling the concentration of involatile solute dissolved in the liquid bath of fill material.

In a further aspect, measurements are performed at different degrees of saturation of the vaporized fill material at the ambient temperature such that all features below a range of maximum feature sizes are filled. The measurements are combined in a multi-target model based measurement to estimate the value of one or more parameters of interest with reduced parameter correlation and improved measurement performance.

Figure 8:
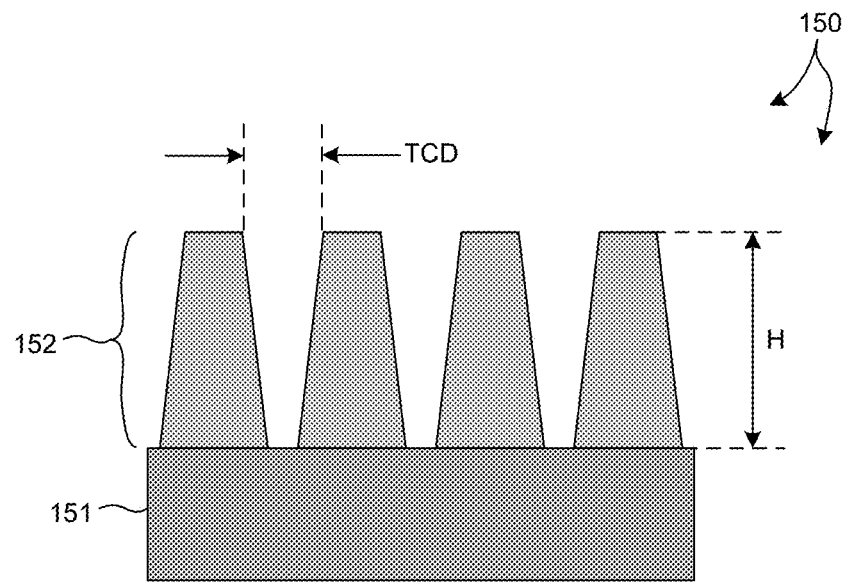
FIG. 8 illustrates an unfilled line-space metrology target having a periodic, two dimensional, resist grating structure fabricated on a substrate.

FIG. 8 illustrates an unfilled line-space metrology target 150 having a periodic, two dimensional, resist grating structure 152 fabricated on a substrate 151. Grating structure 152 has a nominal top critical dimension (TCD) of 7 nanometers and a height, H, of 50 nanometers.

Figure 9:
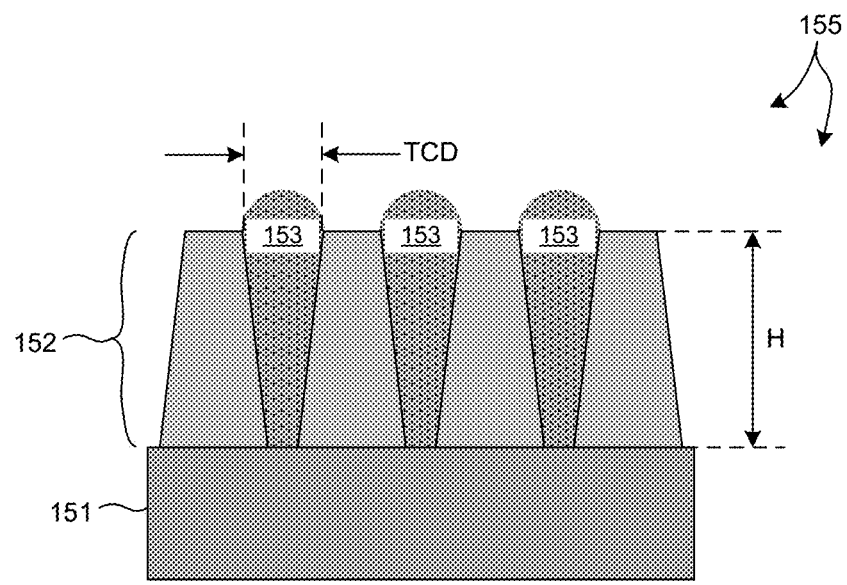
FIG. 9 illustrates the line-space metrology target illustrated in FIG. 8 filled with a fill material.

FIG. 9 illustrates a filled line-space metrology target 155. Line-space metrology target 155 includes the same periodic, two dimensional, resist grating structure 152 fabricated on a substrate 151, however, the spaces between the resist grating structure 152 are filled with a fill material 153. This may be achieved, in one example, by providing gaseous flow 126 to metrology target 155 including toluene at a partial pressure of approximately 70% or higher. In another example, filling of grating structure 152 may be achieved by providing gaseous flow 126 to metrology target 155 including water or ethanol at a partial pressure of approximately 85% or higher.

Figure 10A:
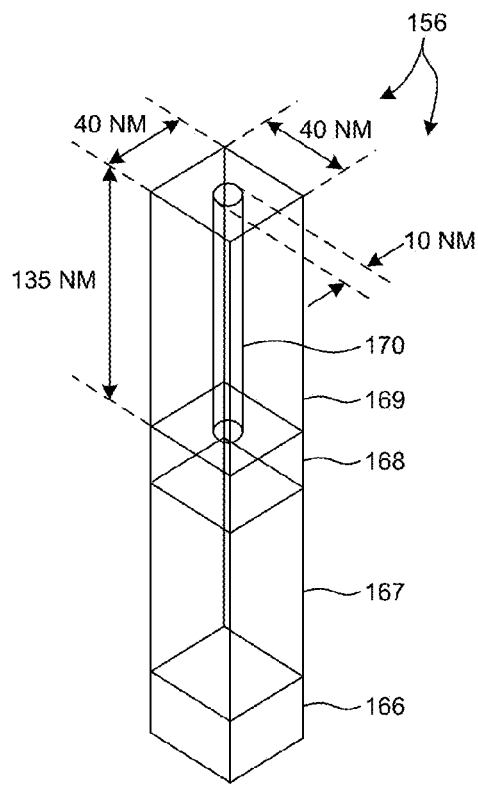
FIG. 10A illustrates an unfilled, metrology target having multiple layers, including a top layer having a cylindrical contact hole.

FIG. 10A depicts an unfilled, metrology target 156 having multiple layers, including a top layer having a cylindrical contact hole. As illustrated in FIG. 10A, metrology target 156 includes a first layer, 166, a second layer, 167, a third layer, 168, and a fourth layer, 169, having a nominal height of 135 nanometers. The fourth layer includes a cylindrical hole feature 170 through the fourth layer having a nominal diameter of 10 nanometers. The structure of metrology target 165 has a nominal width of 40 nanometers and a nominal length of 40 nanometers.

Figure 10B:
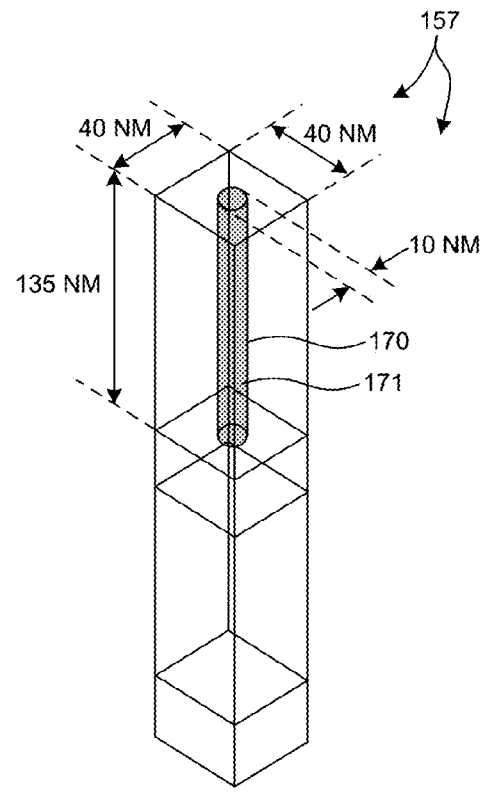
FIG. 10B illustrates the metrology target illustrated in FIG. 10A with the cylindrical contact hole filled with a fill material.

FIG. 10B depicts a filled metrology target 157 including the same metrology target 156, except that the cylindrical hole 170 is filled with an amount of fill material 171. This may be achieved, in one example, by providing gaseous flow 126 to metrology target 156 including toluene at a partial pressure of approximately 85% or higher. In another example, filling of cylindrical hole 170 may be achieved by providing gaseous flow 126 to metrology target 155 including water or ethanol at a partial pressure of approximately 95% or higher.

The metrology targets depicted in FIGS. 8-10B are provided by way of non-limiting example. In general, a measurement site includes one or more metrology targets measured by a measurement system (e.g., metrology system 100 depicted in FIG. 1). In general, measurement data collection may be performed across the entire wafer or a subset of the wafer area. In addition, in some embodiments, the metrology targets are designed for printability and sensitivity to changes in process parameters, structural parameters of interest, or both. In some examples, the metrology targets are specialized targets. In some embodiments, the metrology targets are based on conventional line/space targets. By way of non-limiting example, CD targets, SCOL targets, or AiM™ targets available from KLA-Tencor Corporation, Milpitas, Calif. (USA) may be employed. In some other embodiments, the metrology targets are device-like structures. In some other examples, the metrology targets are device structures, or portions of device structures. Regardless of the type of metrology target employed, a set of metrology targets that exhibit sensitivity to the process variations, structural variations, or both, being explored is measured using shape filling by gaseous adsorption as described herein.

In another aspect, measurement data is collected from CD structures when the CD structures are filled (i.e., subject to gaseous adsorption as described herein) and when they are not filled (i.e., not subject to gaseous adsorption). The collected data is combined in a multi-target model based measurement to improve measurement performance. In one example, measurement data is collected when metrology target 156 is unfilled as depicted in FIG. 10A. In this scenario, a gaseous flow 126 is provided to metrology target 156 without fill material vaporized into the flow. In addition, measurement data is collected when metrology target 156 is filled as depicted in FIG. 10B. In this scenario, a gaseous flow 126 is provided to metrology target 156 with sufficient saturation of fill material to fill cylindrical hole 170 as described with reference to FIG. 10B. The collected data is received by computing system 130. Computing system 130 performs a model based measurement analysis utilizing both sets of measurement data with a multi-target model to estimate the values of parameters of interest. In some examples, the multi-target model described herein is implemented off-line, for example, by a computing system implementing AcuShape® software available from KLA-Tencor Corporation, Milpitas, Calif., USA. The resulting, multi-target model is incorporated as an element of an AcuShape® library that is accessible by a metrology system performing measurements using the multi-target model.

Figure 11:
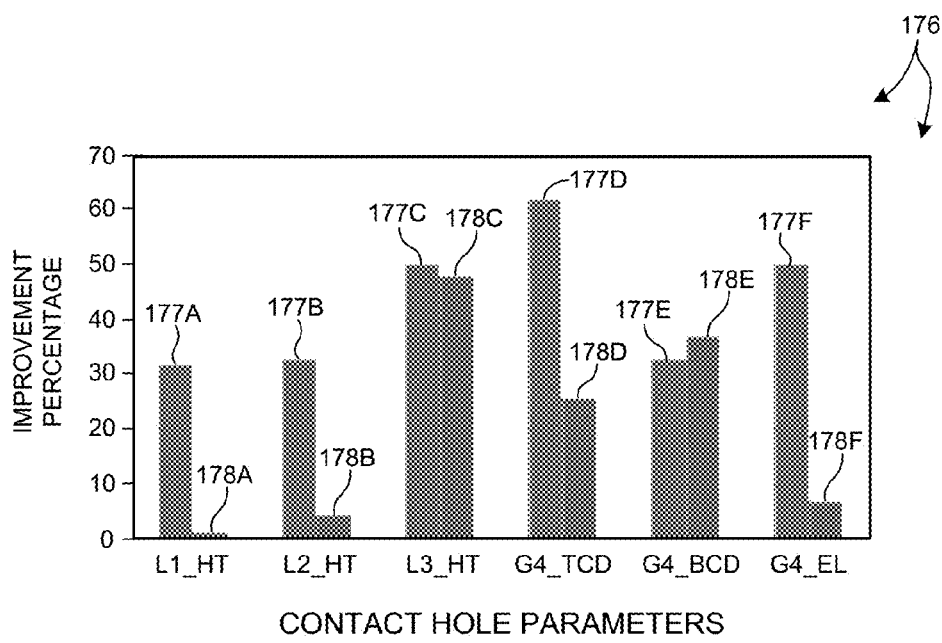
FIG. 11 depicts a comparison of measurement results obtained without shape filling and measurement results obtained with a multi-target model using data collected with and without shape filling for a number of parameters of the metrology target depicted in FIG. 10A.

FIG. 11 depicts a comparison of measurement results obtained without shape filling and measurement results obtained with a multi-target model using data collected with and without shape filling for a number of parameters of metrology target 156 depicted in FIG. 10A. Parameter L1_HT refers to the height of the first layer 166 of metrology target 156 depicted in FIG. 10A. L2_HT refers to the height of the second layer 167. L3_HT refers to the height of the third layer 168. G4_TCD refers to the top critical dimension of cylindrical hole 170. G4_BCD refers to the bottom critical dimension of cylindrical hole 170. G4_EL refers to the ellipticity of cylindrical hole 170. As depicted in FIG. 11, the improvement in measurement precision of each of L1_HT, L2_HT, L3_HT, G4_TCD, G4_BCD, and G4_EL is improved by a significant percentage as illustrated by measurement bars 177A-F, respectively. Similarly, measurement correlation of each of L1_HT, L2_HT, L3_HT, G4_TCD, G4_BCD, and G4_EL is improved (i.e., reduced) by a significant percentage as illustrated by measurement bars 178A-F, respectively.

In another aspect, a series of measurements are performed such that each set of measurement data is collected from metrology target structures when the metrology target structures are filled with a different fill material, or combinations of different fill materials. The collected data is combined in a multi-target model based measurement to reduce parameter correlations and improve measurement performance.

In another aspect, measurement data is collected from a metrology target subject to adsorption when the adsorption process has reached a steady state. In other words, the amount of fill provided by the adsorption process has reached steady state.

In yet another aspect, measurement data is collected from a metrology target subject to adsorption before the adsorption process has reached a steady state. In other words, the amount of fill provided by the adsorption process is changing during the time of measurement.

Figure 12:
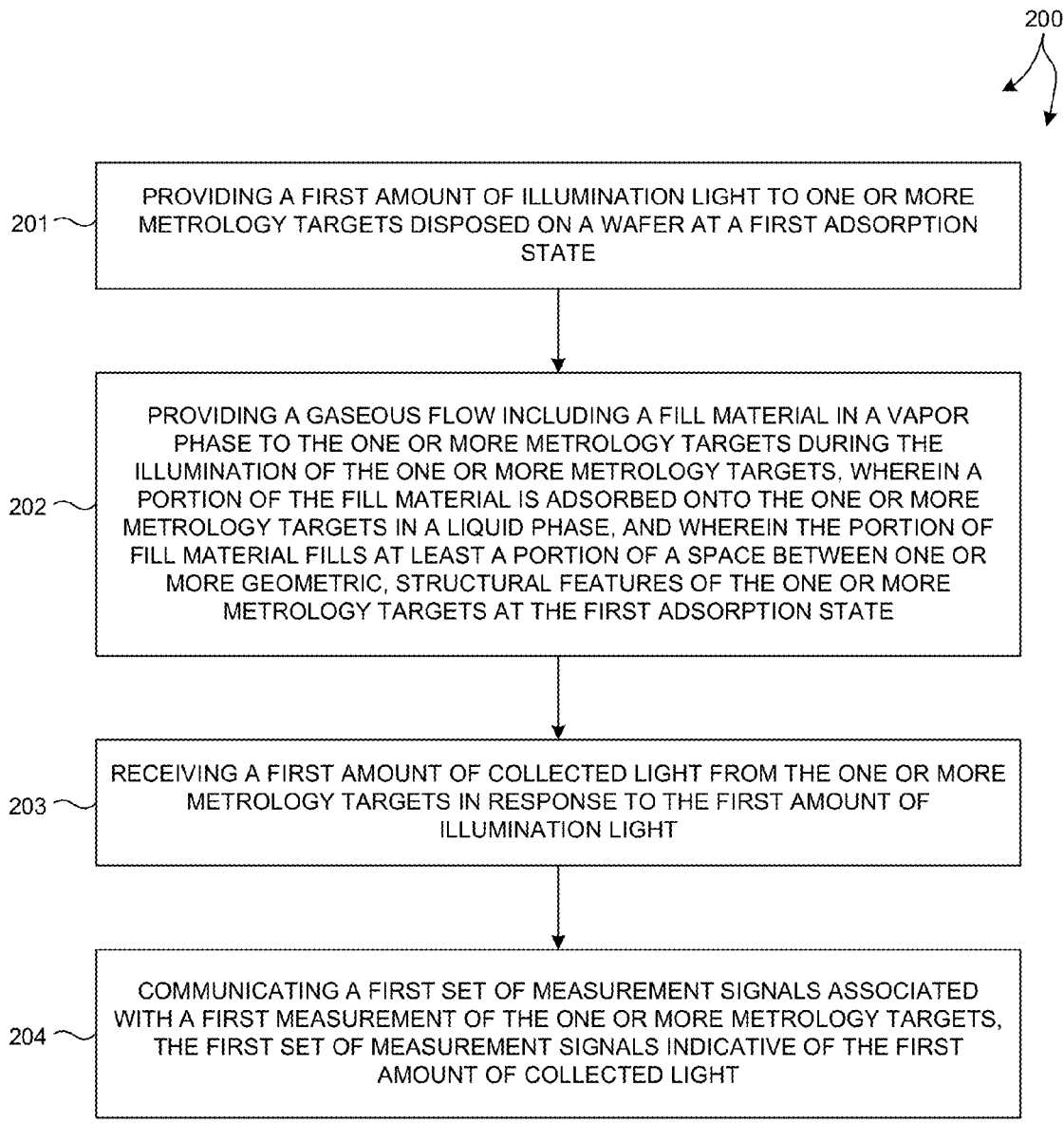
FIG. 12 illustrates a method 200 for performing measurements of structures subject to gaseous adsorption in one example.

FIG. 12 illustrates a method 200 for performing measurements of structures subject to gaseous adsorption. Method 200 is suitable for implementation by a metrology system such as metrology system 100 illustrated in FIG. 1 of the present invention. In one aspect, it is recognized that data processing blocks of method 200 may be carried out via a pre-programmed algorithm executed by one or more processors of computing system 130, or any other general purpose computing system. It is recognized herein that the particular structural aspects of metrology system 100 do not represent limitations and should be interpreted as illustrative only.

In block 201, a first amount of illumination light is provided to one or more metrology targets disposed on a wafer at a first adsorption state.

In block 202, a gaseous flow including a fill material in a vapor phase is provided to the one or more metrology targets during the illumination of the one or more metrology targets. A portion of the fill material is adsorbed onto the one or more metrology targets in a liquid phase, and the portion of fill material fills at least a portion of a space between one or more geometric, structural features of the one or more metrology targets at the first adsorption state.

In block 203, a first amount of collected light is received from the one or more metrology targets by a detector in response to the first amount of illumination light.

In block 204, a first set of measurement signals associated with a first measurement of the one or more metrology targets is communicated, for example, to computing system 130. The first set of measurement signals is indicative of the first amount of collected light.

Figure 13:
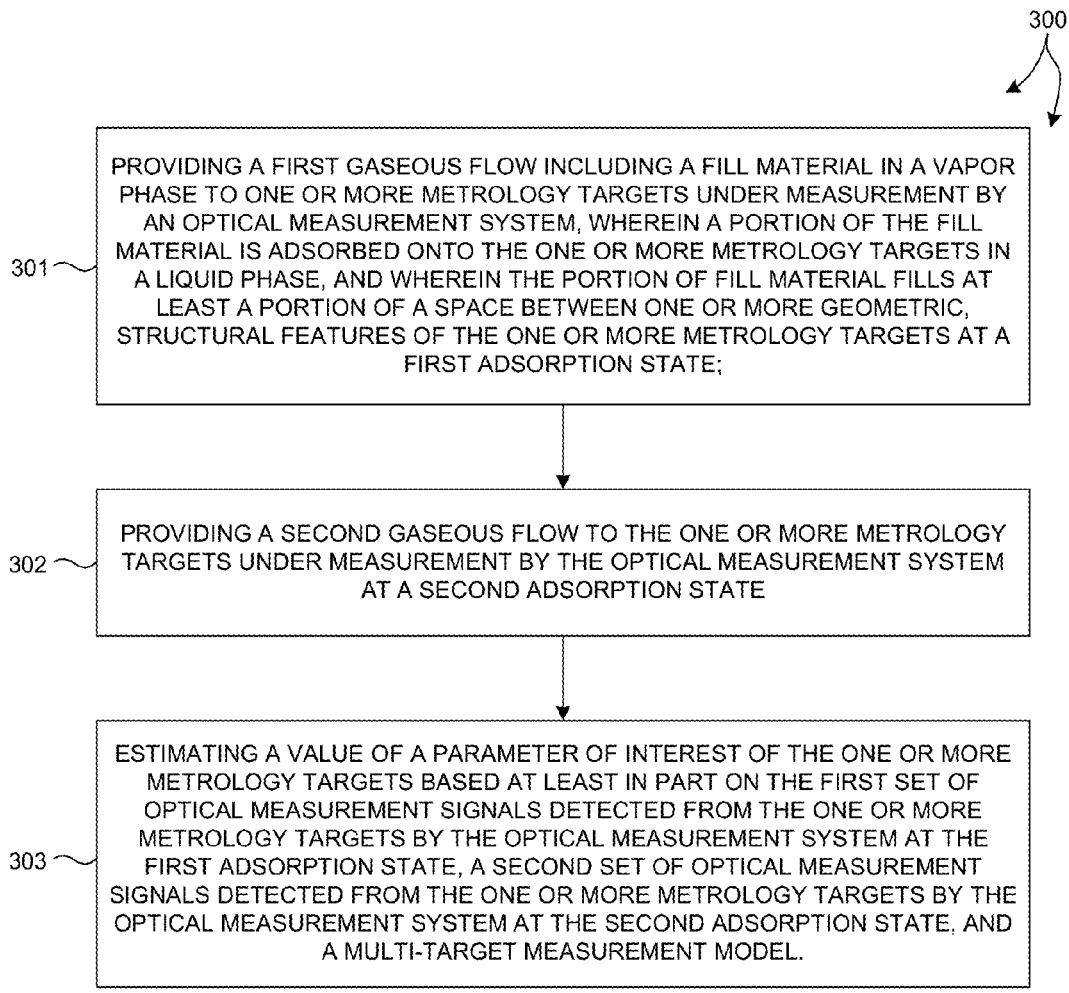
FIG. 13 illustrates a method 300 for performing measurements of structures subject to gaseous adsorption in another example.

FIG. 13 illustrates a method 300 for performing measurements of structures subject to gaseous adsorption in another example. Method 300 is suitable for implementation by a metrology system such as metrology system 100 illustrated in FIG. 1 of the present invention. In one aspect, it is recognized that data processing blocks of method 300 may be carried out via a pre-programmed algorithm executed by one or more processors of computing system 130, or any other general purpose computing system. It is recognized herein that the particular structural aspects of metrology system 100 do not represent limitations and should be interpreted as illustrative only.

In block 301, a first gaseous flow including a fill material in a vapor phase is provided to one or more metrology targets under measurement by an optical measurement system. A portion of the fill material is adsorbed onto the one or more metrology targets in a liquid phase and the portion of fill material fills at least a portion of a space between one or more geometric, structural features of the one or more metrology targets at a first adsorption state.

In block 302, a second gaseous flow is provided to the one or more metrology targets under measurement by the optical measurement system at a second adsorption state.

In block 303, a value of a parameter of interest of the one or more metrology targets is estimated based at least in part on the first set of optical measurement signals detected from the one or more metrology targets by the optical measurement system at the first adsorption state, a second set of optical measurement signals detected from the one or more metrology targets by the optical measurement system at the second adsorption state, and a multi-target measurement model.

In the embodiment depicted in FIG. 1, spectroscopic ellipsometer measurements of metrology targets subject to a gaseous flow having varying amounts of liquid fill material are performed. However, in general, any suitable model-based metrology technique may be employed to perform measurements of metrology targets subject to a gaseous flow having varying amounts of liquid fill material in accordance with the methods and systems described herein.

Suitable model-based metrology techniques include, but are not limited to, spectroscopic ellipsometry and spectroscopic reflectometry, including single wavelength, multiple wavelength, and angle resolved implementations, spectroscopic scatterometry, scatterometry overlay, beam profile reflectometry and beam profile ellipsometry, including angle-resolved and polarization-resolved implementations may be contemplated, individually, or in any combination.

In general, the aforementioned measurement techniques may be applied to the measurement of process parameters, structural parameters, layout parameters, dispersion parameters, or any combination thereof. By way of non-limiting example, overlay, profile geometry parameters (e.g., critical dimension, height, sidewall angle), process parameters (e.g., lithography focus, and lithography dose), dispersion parameters, layout parameters (e.g., pitch walk, edge placement errors), film thickness, composition parameters, or any combination of parameters may be measured using the aforementioned techniques.

By way of non-limiting example, the structures measured with shape filling include line-space grating structures, FinFet structures, SRAM device structures, Flash memory structures, and DRAM memory structures.

In another further aspect, the metrology targets located on the wafer are design rule targets. In other words, the metrology targets adhere to the design rules applicable to the underlying semiconductor manufacturing process. In some examples, the metrology targets are preferably located within the active die area. In some examples, the metrology targets have dimensions of 15 micrometers by 15 micrometers, or smaller. In some other examples, the metrology targets are located in the scribe lines, or otherwise outside the active die area.

In some examples, model-based measurements are performed with shape filling to estimate one parameter of interest. Thus, the measurement model associated with the parameter of interest is optimized independently. By measuring each parameter of interest individually, the computational burden is reduced and the performance of the underlying measurement can be maximized by selecting different wavelengths, measurement subsystems, and measurement methods that are optimized for each individual parameter. In addition, different model-based measurement solvers can be selected, or configured differently, for each parameter of interest.

However, in some other examples, model-based measurements are performed with shape filling to estimate multiple parameters of interest in parallel. Thus, the measurement model is developed to solve for multiple parameters of interest.

In some examples, measurements of parameters of interest performed at a particular measurement site rely on data collected from that particular measurement site only, even though data may be collected from multiple sites on the wafer. In some other examples, measurement data collected from multiple sites across the wafer, or a subset of the wafer is used for measurement analysis. This may be desirable to capture parameter variations across the wafer.

In some examples, measurements of parameters of interest are performed based on filled metrology targets with multiple, different measurement techniques including single target techniques, multi-target techniques and spectra feed-forward techniques. Accuracy of measured parameters may be improved by any combination of feed sideways analysis, feed forward analysis, and parallel analysis. Feed sideways analysis refers to taking multiple data sets on different areas of the same specimen and passing common parameters determined from the first dataset onto the second dataset for analysis. Feed forward analysis refers to taking data sets on different specimens and passing common parameters forward to subsequent analyses using a stepwise copy exact parameter feed forward approach. Parallel analysis refers to the parallel or concurrent application of a non-linear fitting methodology to multiple datasets where at least one common parameter is coupled during the fitting.

Multiple tool and structure analysis refers to a feed forward, feed sideways, or parallel analysis based on regression, a look-up table (i.e., "library" matching), or another fitting procedure of multiple datasets. Exemplary methods and systems for multiple tool and structure analysis is described in U.S. Pat. No. 7,478,019, issued on Jan. 13, 2009, to KLA-Tencor Corp., the entirety of which is incorporated herein by reference.

In yet another aspect, the measurement results obtained as described herein can be used to provide active feedback to a process tool (e.g., lithography tool, etch tool, deposition tool, etc.). For example, values of critical dimensions determined using the methods and systems described herein can be communicated to a lithography tool to adjust the lithography system to achieve a desired output. In a similar way etch parameters (e.g., etch time, diffusivity, etc.) or deposition parameters (e.g., time, concentration, etc.) may be included in a measurement model to provide active feedback to etch tools or deposition tools, respectively. In some example, corrections to process parameters determined based on measured device parameter values may be communicated to a lithography tool, etch tool, or deposition tool.

It should be recognized that the various steps described throughout the present disclosure may be carried out by a single computer system 130, a multiple computer system 130, or multiple, different computer systems 130. Moreover, different subsystems of the system 100, such as the spectroscopic ellipsometer 101, may include a computer system suitable for carrying out at least a portion of the steps described herein. Therefore, the aforementioned description should not be interpreted as a limitation on the present invention but merely an illustration. Further, computing system 130 may be configured to perform any other step(s) of any of the method embodiments described herein.

The computing system 130 may include, but is not limited to, a personal computer system, mainframe computer system, workstation, image computer, parallel processor, or any other device known in the art. In general, the term "computing system" may be broadly defined to encompass any device, or combination of devices, having one or more processors, which execute instructions from a memory medium. In general, computing system 130 may be integrated with a measurement system such as measurement system 100, or alternatively, may be separate, entirely, or in part, from any measurement system. In this sense, computing system 130 may be remotely located and receive measurement data from any measurement source and transmit command signals to any element of metrology system 100.

Program instructions 134 implementing methods such as those described herein may be transmitted over a transmission medium such as a wire, cable, or wireless transmission link. Memory 132 storing program instructions 134 may include a computer-readable medium such as a read-only memory, a random access memory, a magnetic or optical disk, or a magnetic tape.

In addition, the computing system 130 may be communicatively coupled to the spectrometer 104 or the illuminator subsystem 102 of the ellipsometer 101 in any manner known in the art.

The computing system 130 may be configured to receive and/or acquire data or information from subsystems of the system (e.g., spectrometer 104, illuminator 102, vapor injection system 120, and the like) by a transmission medium that may include wireline and/or wireless portions. In this manner, the transmission medium may serve as a data link between the computer system 130 and other subsystems of the system 100. Further, the computing system 130 may be configured to receive measurement data via a storage medium (i.e., memory). For instance, the spectral results obtained using a spectrometer of ellipsometer 101 may be stored in a permanent or semi-permanent memory device (not shown). In this regard, the spectral results may be imported from an external system. Moreover, the computer system 130 may receive data from external systems via a transmission medium.

The computing system 130 may be configured to transmit data or information to subsystems of the system (e.g., spectrometer 104, illuminator 102, vapor injection system 120, and the like) by a transmission medium that may include wireline and/or wireless portions. In this manner, the transmission medium may serve as a data link between the computer system 130 and other subsystems of the system 100. Further, the computing system 130 may be configured to transmit command signals and measurement results via a storage medium (i.e., memory). For instance, the measurement results 115 obtained by analysis of spectral data may be stored in a permanent or semi-permanent memory device (not shown). In this regard, the spectral results may be exported to an external system. Moreover, the computer system 130 may send data to external systems via a transmission medium. In addition, the determined values of the parameter of interest are stored in a memory. For example, the values may be stored on-board the measurement system 100, for example, in memory 132, or may be communicated (e.g., via output signal 115) to an external memory device.

As described herein, the term "critical dimension" includes any critical dimension of a structure (e.g., bottom critical dimension, middle critical dimension, top critical dimension, sidewall angle, grating height, etc.), a critical dimension between any two or more structures (e.g., distance between two structures), and a displacement between two or more structures (e.g., overlay displacement between overlaying grating structures, etc.). Structures may include three dimensional structures, patterned structures, overlay structures, etc.

As described herein, the term "critical dimension application" or "critical dimension measurement application" includes any critical dimension measurement.

As described herein, the term "metrology system" includes any system employed at least in part to characterize a specimen in any aspect, including measurement applications such as critical dimension metrology, overlay metrology, focus/dosage metrology, and composition metrology. However, such terms of art do not limit the scope of the term "metrology system" as described herein. In addition, the metrology system 100 may be configured for measurement of patterned wafers and/or unpatterned wafers. The metrology system may be configured as an inspection tool such as a LED inspection tool, edge inspection tool, backside inspection tool, macro-inspection tool, or multi-mode inspection tool (involving data from one or more platforms simultaneously), and any other metrology or inspection tool that benefits from the calibration of system parameters based on critical dimension data. For purposes of this patent document, the terms "metrology" system and "inspection" system are synonymous.

Various embodiments are described herein for a semiconductor processing system (e.g., an inspection system or a lithography system) that may be used for processing a specimen. The term "specimen" is used herein to refer to a wafer, a reticle, or any other sample that may be processed (e.g., printed or inspected for defects) by means known in the art.

As used herein, the term "wafer" generally refers to substrates formed of a semiconductor or non-semiconductor material. Examples include, but are not limited to, monocrystalline silicon, gallium arsenide, and indium phosphide.

Such substrates may be commonly found and/or processed in semiconductor fabrication facilities. In some cases, a wafer may include only the substrate (i.e., bare wafer). Alternatively, a wafer may include one or more layers of different materials formed upon a substrate. One or more layers formed on a wafer may be "patterned" or "unpatterned." For example, a wafer may include a plurality of dies having repeatable pattern features.

A "reticle" may be a reticle at any stage of a reticle fabrication process, or a completed reticle that may or may not be released for use in a semiconductor fabrication facility. A reticle, or a "mask," is generally defined as a substantially transparent substrate having substantially opaque regions formed thereon and configured in a pattern. The substrate may include, for example, a glass material such as amorphous SiO2. A reticle may be disposed above a resist-covered wafer during an exposure step of a lithography process such that the pattern on the reticle may be transferred to the resist.

One or more layers formed on a wafer may be patterned or unpatterned. For example, a wafer may include a plurality of dies, each having repeatable pattern features. Formation and processing of such layers of material may ultimately result in completed devices. Many different types of devices may be formed on a wafer, and the term wafer as used herein is intended to encompass a wafer on which any type of device known in the art is being fabricated.

In one or more exemplary embodiments, the functions described may be implemented in hardware, software, firmware, or any combination thereof. If implemented in software, the functions may be stored on or transmitted over as one or more instructions or code on a computer-readable medium. Computer-readable media includes both computer storage media and communication media including any medium that facilitates transfer of a computer program from one place to another. A storage media may be any available media that can be accessed by a general purpose or special purpose computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code means in the form of instructions or data structures and that can be accessed by a general-purpose or special-purpose computer, or a general-purpose or special-purpose processor. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk and blu-ray disc where disks usually reproduce data magnetically, while discs reproduce data optically with lasers. Combinations of the above should also be included within the scope of computer-readable media.

Although certain specific embodiments are described above for instructional purposes, the teachings of this patent document have general applicability and are not limited to the specific embodiments described above. Accordingly, various modifications, adaptations, and combinations of various features of the described embodiments can be practiced without departing from the scope of the invention as set forth in the claims.

What is claimed is:

1. A measurement system comprising:
   an illumination source configured to provide a first amount of illumination light to one or more geometric shape features of one or more metrology targets disposed on a wafer at a first adsorption state, the one or more geometric shape features characterized by a critical dimension, the one or more geometric shape features shaped by a semiconductor fabrication process;
   a vapor injection system configured to provide a gaseous flow including a fill material in a vapor phase to the one or more metrology targets during the illumination of the one or more metrology targets, wherein a portion of the fill material is adsorbed onto the one or more metrology targets in a liquid phase, and wherein the portion of fill material fills at least a portion of the one or more geometric shape features of the one or more metrology targets at the first adsorption state; and
   a detector configured to receive a first amount of collected light from the one or more metrology targets in response to the first amount of illumination light and generate a first set of measurement signals indicative of the first amount of collected light.

2. The measurement system of claim 1, further comprising:
   a computing system configured to:
      receive the first set of measurement signals; and
      estimate a value of the critical dimension of the one or more geometric shape features based at least in part on the first set of measurement signals and a measurement model.

3. The measurement system of claim 2, wherein the illumination source is further configured to provide a second amount of illumination light to the one or more metrology targets disposed on the wafer at a second adsorption state that is different from the first adsorption state, wherein the detector is further configured to receive a second amount of collected light from the one or more metrology targets in response to the second amount of illumination light and generate a second set of measurement signals indicative of the second amount of collected light, and wherein the computing system is further configured to:
   receive the second amount of measurement signals; and
   estimate a value of the critical dimension of the one or more geometric shape features based at least in part on the first and second sets of measurement signals and a multi-target measurement model.

4. The measurement system of claim 3, wherein the first amount of illumination light is provided to the one or more metrology targets at a first partial pressure of the fill material and the second amount of illumination light is provided to the one or more metrology targets is performed at a second partial pressure of the fill material.

5. The measurement system of claim 4, wherein the second partial pressure of the fill material is approximately zero.

6. The measurement system of claim 3, wherein the first amount of illumination light is provided to the one or more metrology targets while the fill material is a first fill material and the second amount of illumination light is provided to the one or more metrology targets while the fill material is a second fill material.

7. The measurement system of claim 2, wherein the estimating of the value of the parameter of interest involves any of a model-based regression, a model-based library search, a model-based library regression, image-based analysis, and a signal response metrology model.

8. The measurement system of claim 1, wherein the vapor injection system comprises:
a bubbler including a liquid fill material at a first temperature, wherein a portion of the liquid fill material vaporizes into the gaseous flow provided to the one or more metrology targets, wherein the one or more metrology targets are at a second temperature, higher than the first temperature.

9. The measurement system of claim 1, wherein the vapor injection system comprises:
a bubbler including an involatile solute dissolved in a liquid fill material, wherein a portion of the liquid fill material vaporizes into the gaseous flow provided to the one or more metrology targets.

10. The measurement system of claim 1, wherein the fill material is any of water, ethanol, and toluene.

11. The measurement system of claim 1, wherein the fill material includes multiple, different materials.

12. The measurement system of claim 1, wherein the first amount of illumination light is provided to the one or more metrology targets when an adsorption process has reached a steady state.

13. The measurement system of claim 1, wherein the first amount of illumination light is provided to the one or more metrology targets before an adsorption process has reached a steady state.

14. The measurement system of claim 1, wherein the illumination source and the detector are configured as any of a spectroscopic ellipsometer, a spectroscopic reflectometer, a beam profile reflectometer, a beam profile ellipsometer, or any combination thereof.

15. The measurement system of claim 1, wherein the first amount of illumination includes wavelengths in a range between 120 nanometers and 190 nanometers.

16. A method comprising:
providing a first amount of illumination light to one or more geometric shape features of one or more metrology targets disposed on a wafer at a first adsorption state, the one or more geometric shape features characterized by a critical dimension, the one or more geometric shape features shaped by a semiconductor fabrication process;
providing a gaseous flow including a fill material in a vapor phase to the one or more metrology targets during the illumination of the one or more metrology targets, wherein a portion of the fill material is adsorbed onto the one or more metrology targets in a liquid phase, and wherein the portion of fill material fills at least a portion of the one or more geometric shape features of the one or more metrology targets at the first adsorption state;
receiving a first amount of collected light from the one or more metrology targets in response to the first amount of illumination light; and
communicating a first set of measurement signals indicative of the first amount of collected light.

17. The method of claim 16, further comprising:
receiving the first set of measurement signals; and
estimating a value of the critical dimension of the one or more geometric shape features based at least in part on the first set of measurement signals and a measurement model.

18. The method of claim 16, further comprising:
providing a second amount of illumination light to the one or more metrology targets disposed on the wafer at a second adsorption state that is different from the first adsorption state;
receiving a second amount of collected light from the one or more metrology targets in response to the second amount of illumination light;
generating a second set of measurement signals indicative of the second amount of collected light; and
estimating a value of the critical dimension of the one or more geometric shape features based at least in part on the first and second sets of measurement signals and a multi-target measurement model.

19. The method of claim 18, wherein the first amount of illumination light is provided to the one or more metrology targets at a first partial pressure of the fill material and the second amount of illumination light is provided to the one or more metrology targets at a second partial pressure of the fill material.

20. The method of claim 18, wherein the first amount of illumination light is provided to the one or more metrology targets while the fill material is a first fill material and the second amount of illumination light is provided to the one or more metrology targets while the fill material is a second fill material.

21. The method of claim 16, wherein the providing the gaseous flow involves:
bubbling a purge gas through a bath of the liquid fill material at a first temperature, wherein a portion of the bath of the liquid fill material vaporizes into the gaseous flow provided to the one or more metrology targets, wherein the one or more metrology targets are at a second temperature, higher than the first temperature.

22. The method of claim 16, wherein the providing the gaseous flow involves:
bubbling a purge gas through a bath that includes an involatile solute dissolved in the liquid fill material, wherein a portion of the liquid fill material vaporizes into the gaseous flow provided to the one or more metrology targets.

23. The method of claim 16, wherein the fill material is any of water, ethanol, and toluene.

24. The method of claim 16, wherein the fill material includes multiple, different materials.

25. The method of claim 16, wherein the first amount of illumination light is provided to the one or more metrology targets when an adsorption process has reached a steady state.

26. The method of claim 16, wherein the first amount of illumination light is provided to the one or more metrology targets before an adsorption process has reached a steady state.

27. The method of claim 16, further comprising:
adjusting a degree of saturation of the vaporized fill material such that any spaces between the one or more geometric, structural features below a desired maximum feature size are filled.

28. The method of claim 27, wherein the adjusting of the degree of saturation involves controlling a temperature difference between the one or more metrology targets and a liquid bath of the fill material.

29. A method comprising:
providing a first gaseous flow including a fill material in a vapor phase to one or more metrology targets under measurement by an optical measurement system, wherein a portion of the fill material is adsorbed onto the one or more metrology targets in a liquid phase, and wherein the portion of fill material fills at least a portion of one or more geometric shape features of the one or more metrology targets at a first adsorption state, the one or more geometric shape features characterized by a critical dimension, the one or more geometric shape features shaped by a semiconductor fabrication process;

providing a second gaseous flow to the one or more metrology targets under measurement by the optical measurement system at a second adsorption state; and estimating a value of the critical dimension of the one or more metrology targets based at least in part on the first set of optical measurement signals detected from the one or more metrology targets by the optical measurement system at the first adsorption state, a second set of optical measurement signals detected from the one or more metrology targets by the optical measurement system at the second adsorption state, and a multi-target measurement model.

30. The method of claim 29, wherein the providing the first gaseous flow involves providing the fill material in a vapor phase at a first partial pressure to the one or more metrology targets, and wherein the providing the second gaseous flow involves providing the fill material in a vapor phase at a second partial pressure to the one or more metrology targets.

31. The method of claim 29, wherein the providing the second gaseous flow involves providing a second fill material in a vapor phase to the one or more metrology targets, wherein the second fill material is different from the fill material.

* * * * *